(12) United States Patent
Lyles

(10) Patent No.: US 7,056,332 B2
(45) Date of Patent: Jun. 6, 2006

(54) NUCLEIC ACID BIOMATERIALS AND METHODS OF FORMATION AND USE

(75) Inventor: Mark B. Lyles, Great Lakes, IL (US)

(73) Assignee: Materials Evolution and Development USA, Inc., San Antonio, TX (US)

( * ) Notice: Subject to any disclaimer, the term of this patent is extended or adjusted under 35 U.S.C. 154(b) by 233 days.

(21) Appl. No.: 10/626,793

(22) Filed: Jul. 24, 2003

(65) Prior Publication Data

US 2005/0019369 A1     Jan. 27, 2005

(51) Int. Cl.
*A61B 17/04*   (2006.01)
*A61F 2/00*    (2006.01)
*C07H 21/04*   (2006.01)
*A01N 43/04*   (2006.01)

(52) U.S. Cl. .............. 606/228; 424/426; 536/23.1; 514/44

(58) Field of Classification Search ............ 536/23.1; 435/320.1; 606/228, 229, 231; 514/44
See application file for complete search history.

(56) References Cited

U.S. PATENT DOCUMENTS

| | | | | |
|---|---|---|---|---|
| 5,214,134 | A | | 5/1993 | Weis et al. ............ 536/25.3 |
| 5,245,022 | A | | 9/1993 | Weis et al. ............ 536/24.5 |
| 5,567,810 | A | | 10/1996 | Weis et al. ............ 536/25.3 |
| 5,677,437 | A | | 10/1997 | Teng et al. ............ 536/23.1 |
| 6,093,701 | A | * | 7/2000 | Wolff et al. ............ 514/44 |
| 6,096,722 | A | * | 8/2000 | Bennett et al. ............ 514/44 |
| 6,333,194 | B1 | * | 12/2001 | Levy et al. ............ 435/450 |
| 6,395,029 | B1 | * | 5/2002 | Levy ............ 623/11.11 |
| 6,893,664 | B1 | * | 5/2005 | Burkoth et al. ............ 424/489 |
| 2002/0012694 | A1 | | 1/2002 | Moo-Young et al. ............ 424/449 |
| 2002/0064508 | A1 | | 5/2002 | Lyles ............ 424/59 |
| 2002/0103350 | A1 | | 8/2002 | Lyles ............ 536/23.1 |
| 2003/0044514 | A1 | * | 3/2003 | Richard ............ 427/2.1 |

OTHER PUBLICATIONS

Matthew, Howard W.T., "Polymers for Tissue Engineering Scaffolds", *Polymeric Biomaterials*, Chapter 8, pp. 167–186, 2002.

Chu, C.C., "Textile-Based Biomaterials for Surgical Applications", *Polymeric Biomaterials*, Chapter 19, pp. 491–544, 2002.

PCT International Search Report and Written Opinion of the International Searching Authority of International Application No. PCT/US04/23366, 10 pages, mailing date Jul. 5, 2005.

* cited by examiner

*Primary Examiner*—Richard Schnizer
(74) *Attorney, Agent, or Firm*—Baker Botts L.L.P.

(57) ABSTRACT

Polymers that are biocompatible are useful for various medical purposes such as tissue repair, reconstruction and wound healing. A method and composition for producing a biocompatible polymer formed from nucleic acids is disclosed. The nucleic acid polymer may be used to form a hybrid with an existing polymer to create a copolymer. The nucleic acids may be also be selected to encode particular proteins which may then be expressed in a biological tissue.

5 Claims, 4 Drawing Sheets

NUCLEIC ACID BIOMATERIALS AND METHODS OF FORMATION AND USE

FIELD OF THE INVENTION

The present invention relates to the use of nucleic acids as biomaterials, and more specifically to the use of a nucleic acid as a polymer alone or in combination with a copolymer suitable for use as a biocompatible material.

BACKGROUND OF THE INVENTION

During the last 20 to 30 years, several biocompatible polymers have been developed for use in the body and approved for use by the U.S. Food and Drug Administration (FDA). These FDA-approved materials include polyglycolic acid (PGA), polylactic acid (PLA), Polyglactin 910 (VICRYL®), polyglyconate (MAXON®) and polydioxanone (PDS). Many other biocompatible polymers are under development. In general these materials biodegrade in vivo in a matter of months, although certain forms may biodegrade more slowly. These materials have been used in orthopedic applications, wound healing applications, and extensively as sutures. More recently some of these polymers have also been used in tissue engineering applications.

Tissue engineering is a field that develops tissue products that restore, maintain, or improve tissue function. The need for this approach has arisen out of the lack of suitable donor tissue to repair and restore the body.

In general there are three distinct approaches to engineer new tissue. These are 1) infusion of isolated cells or cell substitutes, 2) use of tissue inducing materials and/or tissue regeneration scaffolds (guided tissue repair) and 3) implantation of cells seeded in scaffolds.

In open scaffold systems and guided tissue repair, tissue engineering materials have normally been fabricated from natural protein polymers such as collagen or from synthetic polymers. These materials often do not have the specific mechanical requirements that a scaffold needs to provide until the new tissue is developed. These materials may also handle poorly, be difficult to suture or may not maintain the desired form or strength for a long enough period of time. Thus it is desirable to develop bioabsorbable and/or biocompatible polymers that extend the range of properties available.

SUMMARY OF THE INVENTION

The present invention includes the use of nucleic acids, particularly DNA, as a polymeric biomaterial. The nucleic acids may be used alone, or as copolymers with other degradable or non-degradable biomaterials. The invention includes such biomaterials, methods of formation and methods of use.

In certain embodiments of the invention, the nucleic acids are used primarily for their biodegradable polymer properties and not for their information coding aspects. However, in other embodiments, both the polymer and information coding aspects of nucleic acids may be used.

One embodiment of the present invention relates to a nucleic acid biomaterial including an isolated, modified nucleic acid.

In other embodiments, the biomaterial includes a suture material or a biomaterial matrix including an isolated, modified nucleic acid.

In another specific embodiment, the biodegradable polymer may be formed a drug carrier or a wound dressing.

More specific embodiments include biomaterial made of at least 50% nucleic acid by weight or volume. Other specific embodiments include biomaterial made of at least 5% 10%, 20%, 30%, 40%, 60%, 70%, 80%, 90%, or 95% nucleic acid by weight or volume In another specific embodiment, the biomaterial may be modified by capping, crosslinking, methylation, ethylation and attachment of a protein or small molecule.

In yet another specific embodiment, the modified nucleic acid comprises at least 5%, 10%, 20%, 30%, 40$, 50%, 60%, 70%, 80%, 90% or 95% DNA per total nucleic acid.

In another specific embodiment, the biomaterial includes a biodegradable copolymer. More specifically, this copolymer may be polylactic acid, polyglycol alginate, polyglycolic acid, poly amino acids, polysaccharides, cellulose acetate, hyaluronic acid and/or collagen.

In other embodiments, the biomaterial may include a hydrogel and/or a tissue scaffold.

In certain embodiments, the nucleic acid of the biomaterial may encode a protein. More specifically, it may include a wound healing factor.

An embodiment of the invention also includes a method of making a biomaterial by purifying a nucleic acid, modifying the nucleic acid and forming a biomaterial from the nucleic acid.

In specific embodiments the biomaterial may be a suture material formed by forming a nucleic acid filament. More specifically, the filament may formed by extruding the isolated nucleic acid through a spinneret and drying the extruded nucleic acid.

In other specific embodiments, the biomaterial may be a biomaterial matrix formed by preparing a solution of the nucleic acid and foaming the solution with supercritical carbon dioxide.

In another specific embodiment, the biomaterial may be a biomaterial matrix formed by freezing an aqueous solution of the nucleic acid and lyophilizing the frozen aqueous solution.

In yet another specific embodiment the biomaterial may be formed by creating a hydrogel including the nucleic acid.

In a specific embodiment, the nucleic acid comprises at least 5%, 10%, 20%, 30%, 40%, 50%, 60%, 70%, 80%, 90% or 95% DNA per total nucleic acid.

In another specific embodiment, the nucleic acid is modified by capping, crosslinking, methylation, ethylation, and/or attachment of a protein or small molecule.

In another specific embodiment a biodegradable copolymer may be added to the modified nucleic acid. More specifically, this biodegradable copolymer may be polylactic acid, polyglycol alginate, polyglycolic acid, poly amino acids, polysaccharides, cellulose acetate, hyaluronic acid and/or collagen.

BRIEF DESCRIPTION OF THE DRAWING

The invention may be better understood by reference to the drawings and detailed description of specific embodiments presented herein.

DETAILED DESCRIPTION OF THE INVENTION

Figure 1:
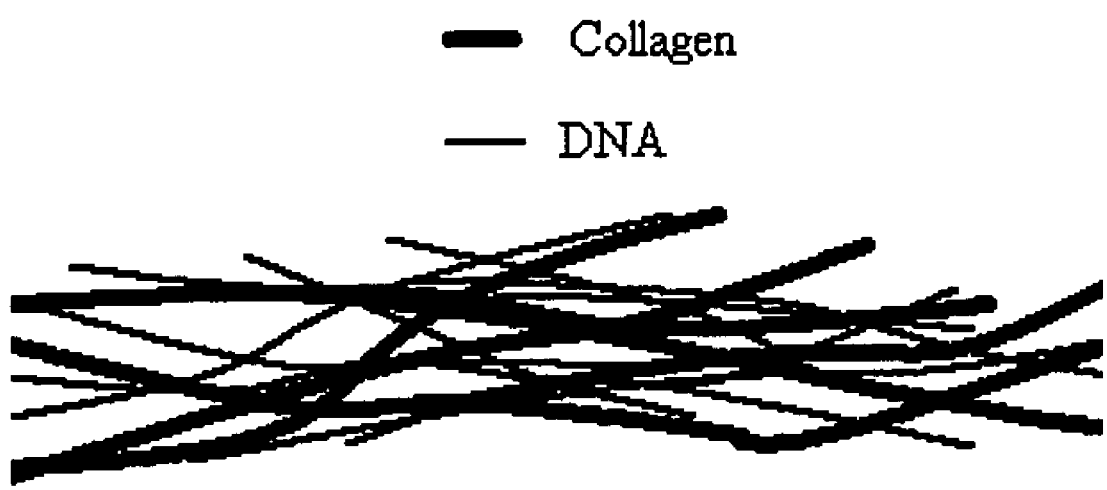
FIG. 1 is a schematic drawing of a collagen/DNA copolymeric suture material according to one embodiment of the present invention.

The present invention broadly relates to the use of nucleic acids as biomaterials, which are biocompatible. Although nucleic acids have been utilized extensively as sources of information, which may be used to produce various biological effects, potential uses based largely upon the polymeric aspects of nucleic acids have been neglected. The present invention capitalizes upon the polymeric properties of nucleic acids, although in certain embodiments it may also relate to their information coding aspects as well.

The present invention encompasses the use of nucleic acids from any source as a polymeric biomaterial. Sources include naturally occurring nucleic acids as well as synthesized nucleic acids. Nucleic acids suitable for use in the present invention include naturally occuring forms of nucleic acids, such as DNA (including the A, B and Z structures), RNA (including mRNA, tRNA, and rRNA together or separated) and cDNA, as well as any synthetic or artificial forms of polynucleotides. The nucleic acids used in the present invention may be modified in a variety of ways, including by crosslinking, intra-chain modifications such as methylation and capping, and by copolymerization. Additionally, other beneficial molecules may be attached to the nucleic acid chains. The nucleic acids may have naturally occurring sequences or artificial sequences. The sequence of the nucleic acid may be irrelevant for many aspects of the present invention. However, special sequences may be used to prevent any significant effects due to the information coding properties of nucleic acids, to elicit particular cellular responses or to govern the physical structure of the molecule.

Nucleic acids may be used in a variety of crystalline structures both in finished biomaterials and during their production processes. Nucleic acid crystalline structure may be influenced by salts used with the nucleic acid. For example, Na, K, Bi and Ca salts of DNA all have different precipitation rates and different crystalline structures. Additionally, pH influences crystalline structure of nucleic acids.

The physical properties of the nucleic acids may also be influenced by the presence of other physical characteristics. For instance, inclusion of hairpin loops may result in more elastic biomaterials or may provide specific cleavage sites.

The nucleic acid polymers and copolymers produced may be used for a variety of tissue engineering applications including, inter alia, to increase tissue tensile strength, improve wound healing, speed up wound healing, as templates for tissue formation, to guide tissue formation, to stimulate nerve growth, to improve vascularization in tissues, as a biodegradable adhesive, as device or implant coating, or to improve the function of a tissue or body part. The polymers may also more specifically be used as sutures, scaffolds and wound dressings. The type of nucleic acid polymer or copolymer used may affect the resulting chemical and physical structure of the polymeric biomaterial.

1. Sources of Nucleic Acids

Naturally occurring nucleic acids may be harvested from almost any biological material. Harvesting techniques, including those capable of producing commercial volumes of nucleic acids (including nucleic acids with a specific sequence or group of sequences) are known in the art. Nucleic acids may be extracted from almost any biological source. Two common sources of non-specific DNA are fish sperm and calf thymus. Almost any source, animal or plant-based, yeast or bacterial may be used. These sources may be specifically developed for nucleic acid harvest or may be waste products of other commercial processes, as in the case of calf thymus.

Because many embodiments of the invention employ nucleic acids for their polymeric properties alone, and not their information coding properties, the sequences of nucleic acids may be irrelevant in such applications. However, it is possible that a given source may be undesirable because the nucleic acid retains its information coding aspects, which may give rise to unwanted side effects. For instance, in some examples it may be desirable to avoid use of bacterial nucleic acid sources if there is a danger of transformation of local bacteria with new sequences as the nucleic acid polymer degrades. Similarly, it may be best to use plant-derived nucleic acids in some applications in mammals to avoid transcription or translation of mammalian nucleic acids formed by polymer breakdown. Additionally, specific sequences may be desirable to product certain physical effects, such as hairpin loops.

In other aspects of the present invention it may be desirable for nucleic acids to become accessible for transcription or translation either in the form of the initially supplied polymeric biomaterial or as breakdown products thereof. For instance, the nucleic acids may encode proteins useful in association with the biomaterial, such as cytokines or wound healing factors. These proteins may be produced in mammalian cells or in bacteria resident around the biomaterial. They may promote an activity in mammalian tissue, result in destruction of unwanted bacteria, or have other benefical effects.

Nucleic acids, in certain examples, may be produced by solubilization of cellular material with a detergent, followed by extraction of nucleic acids from the aqueous layer with an alcohol. Various additional steps and additives may assist in the removal of protein to obtain purer nucleic acids. RNase inhibitors may be used to obtain better RNA yield. Various nucleases and extraction techniques may be employed to destroy unwanted forms of nucleic acids, such as RNA in a DNA sample. Such techniques are well known in the art. Techniques for obtaining nucleic acids of a given sequence or sequences are also known.

Nucleic acids may also be synthesized artificially from nucleotides. For instance, surface catalysis techniques or oligonucleotide synthesizers may be used. Artificial nucleic acids allow for ready control of sequence. This may be significant in avoiding unwanted side effects, or for obtaining beneficial effects as described above.

2. Capping, Crosslinking and Nucleic Acid Modifications

Nucleic acids have different rates of degradation, which may be modified and exploited. Additionally, particular degradation products may be desired (for instance, nucleic acids with a given sequence). The sites or timing of degradation may be modified so as to obtain these products.

First, the type of nucleic acid selected may affect degradation. RNA will likely degrade much more rapidly than DNA. Different DNA structures may have different degradation rates. This may also vary by the tissue in which the nucleic acid is used. Various disease states or injuries may also affect degradation.

Second, in particular embodiments of the present invention, purified nucleic acids may be cross-linked to reduce degradation. Cross-linking may be accomplished in a variety of ways, including hydrogen bonds, ionic and covalent bonds, ππ bonds, polarization bonding, van der Wals forces.

More specifically, crosslinking may be accomplished by UV radiation, esterification, hydrolysis, intercalating agents, neoplastic agents, formaldehyde, formalin, or silica compounds. One specific example includes the use of siloxane bridges as described in U.S. Pat. No. 5,214,134.

More than one type of crosslinking may be used within a given biomaterial. For example, use of a type of crosslinking easily degraded in a cell coupled with a more degradation resistant type of crosslinking may result in a biomaterial that is opened in two phases, one when the easily degraded crosslinks are broken and second when the more resistant crosslinks or the nucleic acid itself are degraded.

Crosslinking may occur between two strands of a double stranded nucleic acid or between the strands of two separate double strands. It may also occur between two separate single strands. Double strand to single strand crosslinking is also possible, as is crosslinking between different regions of one strand. Increased levels of crosslinking will generally slow degradation of nucleic acids. Linkers such as small organic molecules (esters, amines) or inorganic molecules (silicas, siloxanes), including microparticles or nanoparticles thereof, may be used to attach copolymers to nucleic acids.

Third, nucleic acids may be methylated, ethylated, alkylated, or otherwise modified along the backbone to influence degradation rates. Generally, methylated, hemi-methylated, ethylated, or alkylated nucleic acids will degrade more slowly. Other backbone modifications affecting degradation rates include the use of heteroatomic oligonucleoside linkages as described in U.S. Pat. No. 5,677,437. Additionally, modifications may be used to prevent the nucleic acid from being transcribed or translated in a given tissue or organism.

Fourth, nucleic acids may be capped to prevent degradation. Such caps are generally located at or near the termini of the nucleic acid chains. Examples of capping procedures are included in U.S. Pat. Nos. 5,245,022 and 5,567,810. In specific embodiments of the present invention, inorganic caps are used.

3. Copolymerization

Biomaterials of the present invention also include copolymers. Copolymers that are also biodegradable and non-toxic to mammals may be preferred. However, polymers in which only one polymer (e.g. the nucleic acid portion) degrades, leaving a non-biodegradable framework may also be desirable in certain situations.

Examples of biomaterials that may be used as copolymers with nucleic acids include, but are not limited to, poly(amino acids), including PGA, PLA, PLGA and poly(proline), polysaccharides, such as cellulose, chitin and dextran, proteins, such as fibrin and casein, VICRYL®, MAXON®, PDS, poly(e-caprolactone), polyanhydirdes, trimethylene carbonate, poly(β-hydroxybutyrate), poly(DTH imino carbonate), poly(bisphenol A iminocarbonate), poly(ortho ester), polycyanoacrylate, polyphospohazene and hyaluronic acid.

Polymers may be formed in a variety of ways, depending upon the copolymer used and the desired properties of the finished polymer. The copolymer may be attached to the nucleic acid by covalent, ionic or hydrogen bonds or by Van der Wals forces. Linkers such as small organic molecules (esters, amines) or inorganic molecules (silicas, siloxanes), including microparticles or nanoparticles thereof, may be used to attach copolymers to nucleic acids. The finished biomaterial may contain the nucleic acids and copolymers arranged in a variety of fashions including, substantially end-to-end, end-to-side, side-to-side, or any mixture thereof with one or more linkages securing such attachments. Copolymers may also fall into the general forms or block copolymers and graft copolymers.

The nucleic acids in such copolymers may be selected or treated as described above for nucleic acid polymers.

4. Polymer Modifications and Additions

Chemical and biological properties of nucleic acid polymers of the present invention may be influenced by modifications of the polymers, such as modification of the hydrophobicity or hydrophilicity of the polymers or copolymers. Additionally, any inorganic or organic molecules, including amino acids, silicas, cytokines, such as interleukins, biologics and drugs may be added to the nucleic acid polymers to produce certain biological effects. Nucleic acids provide a variety of molecular attachment sites and therefore facilitate covalent, ionic and hydrogen bonding, as well as Van der Wals attachments, or other forms of attachment.

5. Sutures and Filamentous Biomaterials

Polymers of the present invention may be used to form filamentous polymeric biomaterials. Nucleic acids are filamentous by nature. This may allow formation of sutures or thread-like biomaterials simply by crosslinking nucleic acids. Techniques to draw the polymers into a filamentous form may also be used. Filament formation techniques may be particularly advantageous where a copolymer in the filament is not naturally filamentous. Such techniques include those known in the art for preparation of polymer filaments. Embodiments of filamentous polymers may be extruded, precipitated, woven and monofilamentous, inter alia. In specific embodiments, extrusion methods are used to produce filamentous biomaterials.

Formation of filamentous nucleic acid polymers may be facilitated by methods in which crosslinking, copolymerization, or other processes that define the overall structure of the polymer are not complete until after filament formation.

In one embodiment of the invention, the filamentous nucleic acid polymers may be used to form sutures. Filaments may used as initially produced or they may be twisted or braided, as is common in suture preparation. The composition of the nucleic acid polymers may be varied depending upon the length of time such sutures need to remain intact. Additionally, the sutures may be designed to produce bacteriocidal or healing factors as they degrade, or may be initially coated with such factors. Other treatment methods in use with other suture material may also be applied to sutures of the present invention.

6. Structural Biomaterials

Polymers of the present invention may also be shaped into structural biomaterials, such as sponge-like forms for tissue growth or dental implants. Such structures may be formed using current methods for manipulation of biological materials, such as extracellular matrix material. They may also be formed by supplying the nucleic acid polymer to a mold or form before it is completely set in its final polymerized, crosslinked or other end state.

Structural biomaterials may include or produce as breakdown products a number of biological factors. For instance, angiogenic factors may be used to induce vascularization of tissue growing in the structural biomaterial. Structural biomaterials, in particular, may benefit from a multi-stage degradation wherein a certain crosslinker or other bond is broken early after introduction of biological cells or tissues or placement in a patient, but other crosslinkers or bonds retain the basic structure until sometime later.

Structural, wound healing and other biomaterials of the present invention may also be formed using a variety of techniques also used for other biomaterials. In particular embodiments, extrusion techniques may be used. For example, a spongelike biomaterial may be formed using a rotating extrusion device.

7. Wound Healing Biomaterials

Polymers of the present invention may be used for wound healing in a variety of ways. First, nucleic acid polymers may be used to form hydrogels for use in a wound. They may also be shaped into patches or dressings to be placed in or over wounds.

A hydrogel is typically a three-dimensional network of polymers held together by association bonds. These networks are able to hold a large quantity of water within their structure without dissolving. They may have superior chemical and physical properties such as increased elasticity. The polymer portions of hydrogels may be formed first, with the aqueous components added later to allow easier transport, and more flexibility in terms of the solution added. For instance, an aqueous solution with a soluble drug may be used to hydrate the hydrogel. The desired soluble drug may vary for a given application. Hydrogels may also be in the form of a polywater, in which substantially all water in the hydrogel is in association with the nucleic acid polymer and accordingly limited in its movement.

Wound dressings may be formed as patches or 3D structures and they may be woven from filamentous nucleic acid polymers. Wound dressings in particular may benefit from the inclusion of bacteriocidal, clotting, or other factors on the nucleic acid polymers. Wound dressings intended to remain in place may encode healing factors, which may be designed to become expressible at particular stages of polymer degradation and wound healing. Wound dressing may also be formed from polywater hydrogels.

8. Other Biomaterials

The present invention includes the use of nucleic acids polymers as any sort of degradable biomaterial. Such materials may be used in vitro or in vivo. They may be modified in any manner typical of other biodegradable materials for a given use.

Specifically, the nucleic acid polymers of the present invention may also be used as adhesives, drug carriers, coatings for surgical pins and plates or other materials, inhalers, fillers, membranes, cloths, castings, implants and as any other type of biocompatible material. In specific embodiments, nucleic acid biomaterials may be processed in any way PVA is processed and may be put to similar uses.

Water content of the various biomaterials of the present invention may be altered depending upon the intended use. For example, if the biomaterials are to be used as a wound dressing, water content may be at least 90%. For sutures water content may be as low as 5% or lower. In general water content may be similar to that of other materials put to similar uses.

The following examples are provided to illustrate certain aspects of the present invention. They are not intended to encompass and fully describe the entire invention or any aspect thereof.

EXAMPLES

Example 1

DNA-Based Suture Material

Suture material according to one embodiment of the present invention may be prepared using waste DNA. Such DNA may be harvested from calf thymus, fish sperm or other animal waste. It may be extracted from plant waste such as spoiled vegetation.

The tissue may be solubilized by first processing it to a pulp, then adding a detergent such as SDS. Proteinases such as Proteinase K may be added to destroy excess protein. RNases may be added to destroy RNA in the sample.

DNA may be extracted by adding Tris-phenol/chloroform or chloroform/isoamylalcohol. Approximately 70% or greater alcohol, such as ethanol or methanol may also be used to extract DNA. If phenol or isoamylalcohol are used to extract the DNA it may be lyophilized to help remove residual chemical.

Extracted DNA may be washed by repeated solubilization in water and extraction with alcohol to remove additional protein components. Special steps in which proteinases and RNases are added under digestion conditions may also aid in enhancing DNA purity.

For longer lasting sutures, the DNA may be crosslinked, capped and methylated or ethylated. It may also be treated by other methods described above to increase degradation resistance.

After any degradation resistance treatments, the DNA may be suspended in an aqueous solution with low alcohol content to form a viscous gel. This gel may then be extruded a spinneret similar to those used in collagen processing into a solution which causes DNA to condense, such as a high-alcohol content aqueous solution. DNA filaments thus formed may then be collected from the solution and dried.

The alcohol contents of the low-alcohol content and high-alcohol contents solution may vary depending upon whether the DNA is treated to reduce degradation. For untreated DNA the low-alcohol content aqueous solution may be approximately between 5 and 30% alcohol. The high-alcohol content solution may be between 80 and 95% alcohol.

The DNA filaments may be twisted or braided in the same manner as other suture filaments to produce stronger and more durable suture material.

Example 2

DNA/Collagen-Based Suture Material

DNA may be prepared and treated as described above. DNA in an aqueous solution of approximately 30% alcohol or less and containing little to no residual proteinase may then be crosslinked with collagen. The DNA solution be selected to contain DNA of only a certain molecular weight range.

Collagen may be prepared from animal tendons such as the flexor tendons of cattle. The tendons are cleaned, frozen, sliced and treated with ficin. They are then swollen with dilute cyanoacetic acid to produce a viscous gel. The DNA solution may be added to this gel along with a crosslinking agent such as 4% paraformaldehyde, or the gel may be subjected to ultraviolet radiation in order to crosslink the DNA and collagen. For many applications of the present invention, the crosslinking agent or method should be selected so that toxic by products will not be formed during degradation of the suture material.

The crosslinked solution may then be extruded through a spinneret into an aqueous solution containing high levels of acetone and alcohol, in which it will condense into fibers that may be dried. See FIG. 1.

This general scheme may also be used with other polypeptides such as poly(amino acids) or hydrogenated keratins. Additionally, PVA may be used in place of or in addition to the polypeptides.

Example 3

DNA-Based Tissue Scaffold

DNA may be prepared as described in Example 1. The viscous solution of DNA may be resuspended in an aqueous solution with alcohol content between approximately 5 to 20%. This solution may then be poured into an appropriately shaped mold and frozen. Alcohol can then be evaporated from the frozen material. The solution may then be lyophilized to leave a porous material formed from the DNA. Exclusion of the DNA from the solvent crystal phase leaves a porous skeleton of material. The pore size of the material may be varied by varying the rate of freezing and the alcohol content. Freezing methods that result in larger crystals tend to produce larger pores. Additionally, temperature gradients in the frozen solution can be used to produce a material with a gradient of pore sizes.

In an alternative procedure, the DNA solution may be dried in the presence of supercritical carbon dioxide, which acts as a foaming agent.

Membranes such as these may be used for guided tissue regeneration, including tissue regeneration in patients. For instance, they may be used in applications where bone must grow below the membrane and fibroblasts on top. Using current technology, the membrane must usually be removed one regeneration has begun. This results in additional danger and discomfort to the patient. Membranes of the present invention may be designed to degrade at appropriate times, eliminating the need for removal.

Example 4

Hydrogel Formation

Figure 2:
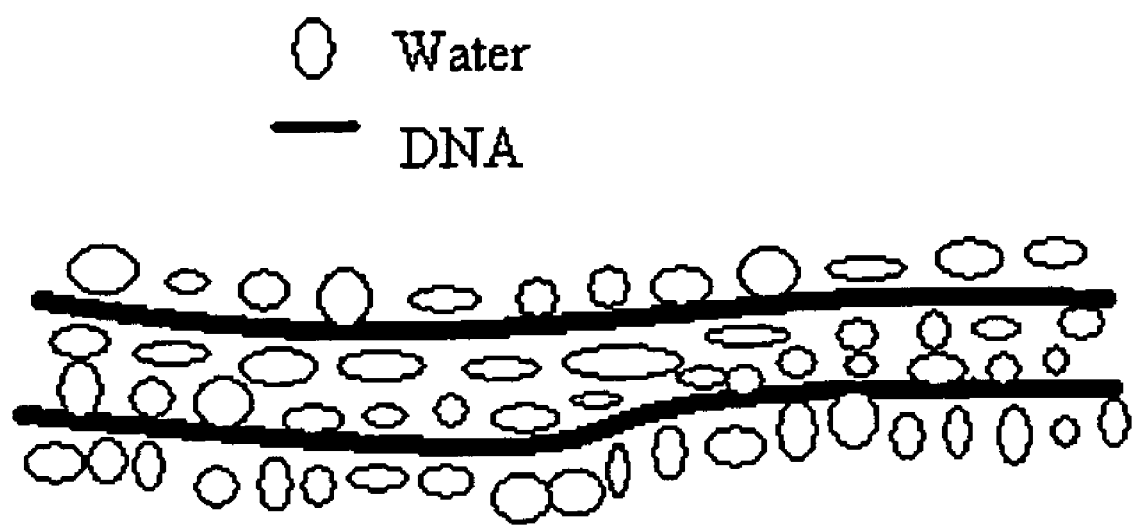
FIG. 2 is a schematic drawing of a DNA polywater biomaterial according to one embodiment of the present invention. All water molecules are not shown in the drawing.

Hydrogels based on DNA may be formed with techniques used to produce polywater with PVA. See FIG. 2. Essentially, a solution of about 20% DMSO, 79% water and 1% DNA by volume may be prepared and frozen. In the frozen state, a shell of water forms around the DNA molecules, which tend to be evenly spaced. DMSO and water may then be removed so that the only water substantially held in place around the DNA remains. This results in a composition of up to 99% water by volume, but with very little free water. This produces a substance that is capable of retaining moisture while allowing exchange of gasses. Such a substance may be formed into a membrane and used as a wound dressing.

Example 5

Silica-Based Nucleic Acid Biomaterials

Figure 3:
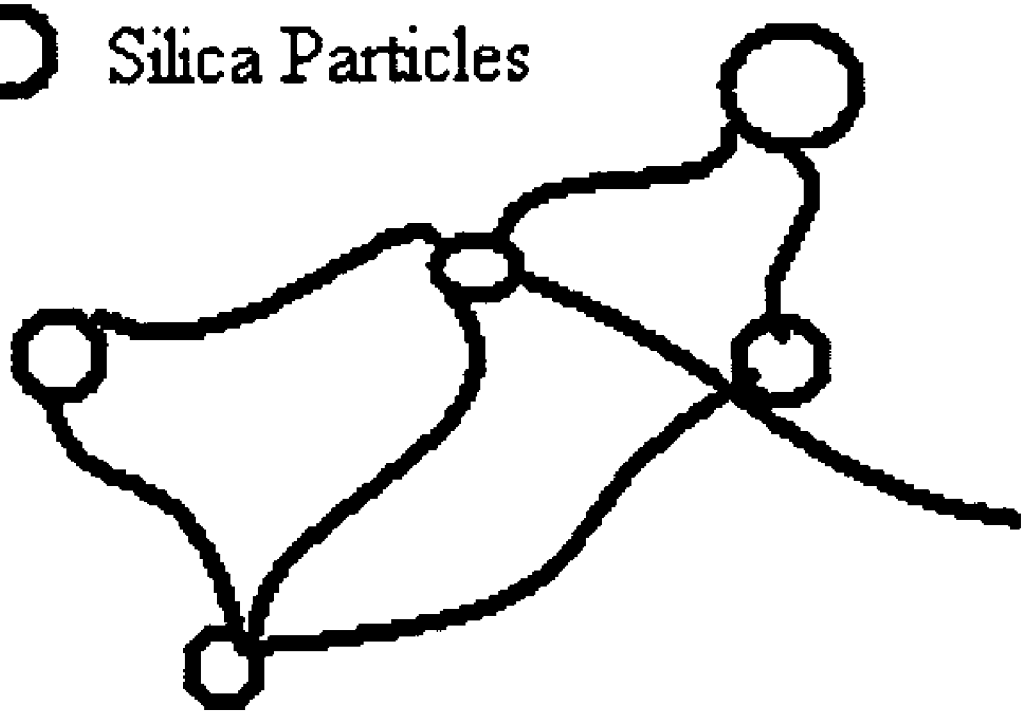
FIG. 3 is a schematic drawing of a silica/DNA biomaterial according to one embodiment of the present invention.

Biomaterials of the present invention may also be formed by bonding DNA or other nucleic acids to silica particles. In specific embodiments the DNA may bond substantially at the end of the DNA molecule. The DNA molecule may be bound to a silica particle at either end and possibly at other points along the DNA strand. Multiple DNA molecules may be bound to a silica particle. Example embodiments may contain up to 50% silica by weight or volume. See FIG. 3.

Figure 4:
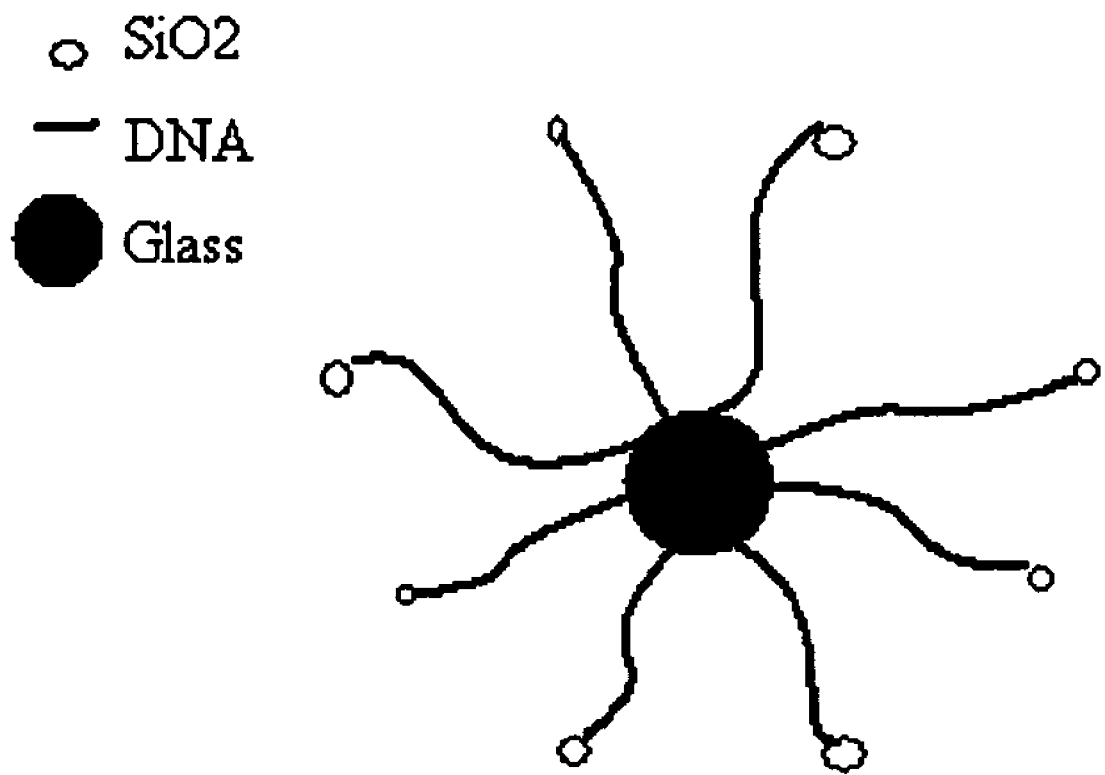
FIG. 4 is a schematic drawing of a silica/glass/DNA biomaterial according to one embodiment of the present invention.

In another embodiment, DNA may be bonded at one end to a glass microparticle, such as a 1 μm diameter glass fiber, with the other end of each DNA molecule bonded to an $SiO_2$ nanoparticle, such as a 1 nm diameter particle. See FIG. 4.

Biomaterials of the present invention additionally include nucleic acids coated on silica surfaces.

Example 6

Wound Dressings Containing TNFα

Hypertrophic scarring is a significant problem in many types of wounds, especially burns. Research indicates that hypertrophic scar tissue contains abnormally low levels of TNFα when compared to normal scar tissue. Hydrogels are commonly used to treat burns and sometimes lead to less scarring, but presently available hydrogels are unable to address the TNFα deficiencies that lead to hypertrophic scarring.

To address this problem, a hydrogel containing TNFα may be prepared using the DNA as described in Example 1. The DNA may be formulated into a hydrogel by suspension in an aqueous solution of no more than approximately 20% alcohol. Prior to hydrogel formation, TNFα may be linked to the DNA using a degradable crosslinker or bond, such as an ester bond. The strength and nature of this bond or crosslink will determine the rate of TNFα release. Additionally, multiple types of bonds or crosslinks may be used to obtain an even longer time-frame of TNFα release.

Other proteins may also be incorporated in the wound dressing. Such proteins include growth factors such as FGF, EGF and VEGF, fibronectin, vitronectin, adhesion factors and steroids. These and other proteins may be added to various other biomaterials of the present invention.

Example 7

Wound Dressing Encoding TNFα

A wound dressing DNA hydrogel may be prepared as described above. However, the DNA used for the hydrogel may be specifically selected to encode TNFα with an operable promoter. Such specific DNA may be prepared using any methods known to the art. Preparation of DNA in a mammalian or even yeast cell bioreactor may be preferable to the use of a bacterial source to limit the possibility of endotoxins. The DNA may also be treated to facilitate uptake by cells.

Example 8

Drug Encapsulation

DNA prepared according to the methods of the present invention may also be used as a drug encapsulent. It may be used as a spray, film, membrane or solid bead. For example, the nucleic acid may be partially solubilized in alcohol such as ethanol, acetone or a volatile organic solvent then sprayed onto the drug and the solvent then evaporated. It may also be foamed using a carbon dioxide agent.

Example 9

Delivery Agent

Nucleic acid polymers of the present invention may also serve as delivery agents for other materials. This may be their primary function or an additional function. Materials may be delivered by or absorption onto the surface of the nucleic acid biomaterial. For instance, the biomaterial may contain on its surface antibiotics, antioxidants, antivirals and/or growth factors, inter alia.

Example 10

DISPENSATION

Nucleic acid biomaterials of the present invention may be formed into shapes as described above. They may also be provided in saline solutions, buffered solutions, alcohol solutions, DMSO solutions and other solutions. These solutions may be designed to promote stability during storage.

Although only exemplary embodiments of the invention are specifically described above, it will be appreciated that modifications and variations of the invention are possible without departing from the spirit and intended scope of the invention.

What is claimed is:

1. A method of making a suture material comprising:
   a) isolating a nucleic acid;
   b) modifying the nucleic acid:
   c) suspending the modified nucleic acid in an aqueous solution and adding sufficient alcohol to the solution to form a viscous gel comprising the modified nucleic acid;
   d) forming a nucleic acid filament by extruding the viscous gel through a spinneret into a solution that causes nucleic acids to condense into a filament; and
   e) drying the extruded nucleic acid filament to form said suture material.

2. The method of claim 1, wherein the nucleic acid comprises at least 95% DNA per total nucleic acid.

3. The method of claim 1, wherein the modifying comprises at least one technique selected from the group consisting of: capping, crosslinking, methylation, ethylation, and attachment of a protein or molecule.

4. The method of claim 1, further comprising adding a biodegradable polymer to the modified nucleic acid.

5. The method of claim 4, wherein the biodegradable polymer is selected from the group consisting of: polylactic acid, polyglycol alginate, polyglycolic acid, poly amino acids, polysaccharides, cellulose acetate, hyaluronic acid and collagen.

* * * * *